United States Patent
Wong et al.

(10) Patent No.: US 8,163,937 B2
(45) Date of Patent: Apr. 24, 2012

(54) PROCESS FOR PREPARING (1R,2S,5S)-N-[(1S)-3-AMINO-1-(CYCLOBUTYLMETHYL)-2,3-DIOXOPROPYL]-3-[(2S)-2-[[[(1,1-DIMETHYLETHYL)AMINO]-CARBONYL]AMINO]-3,3-DIMETHYL-1-OXOBUTYL]-6,6-DIMETHYL-3-AZABICYCLO[3.1.0]HEXANE-2-CARBOXAMIDE

(75) Inventors: George S. K. Wong, Summit, NJ (US);
Hong-Chang Lee, Livingston, NJ (US);
Jennifer A. Vance, Scotch Plains, NJ (US);
Weidong Tong, Mountainside, NJ (US);
Tetsuo Iwama, Scotch Plains, NJ (US)

(73) Assignee: Schering Corporation, Kenilworth, NJ (US)

( * ) Notice: Subject to any disclaimer, the term of this patent is extended or adjusted under 35 U.S.C. 154(b) by 196 days.

(21) Appl. No.: 12/519,485

(22) PCT Filed: Dec. 18, 2007

(86) PCT No.: PCT/US2007/025804
§ 371 (c)(1),
(2), (4) Date: Feb. 1, 2010

(87) PCT Pub. No.: WO2008/079216
PCT Pub. Date: Jul. 3, 2008

(65) Prior Publication Data
US 2010/0145013 A1    Jun. 10, 2010

Related U.S. Application Data

(60) Provisional application No. 60/876,447, filed on Dec. 20, 2006.

(51) Int. Cl.
*C07D 209/52* (2006.01)
(52) U.S. Cl. ......................................................... 548/515
(58) Field of Classification Search ........................ None
See application file for complete search history.

(56) References Cited

U.S. PATENT DOCUMENTS

| | | |
|---|---|---|
| 7,012,066 B2 | 3/2006 | Saksena et al. |
| 2003/0216325 A1 | 11/2003 | Saksena et al. |
| 2005/0059800 A1 | 3/2005 | Sudhakar et al. |
| 2005/0249702 A1* | 11/2005 | Njoroge et al. .............. 424/85.4 |

* cited by examiner

*Primary Examiner* — Yong Chu
*Assistant Examiner* — Michael Barker
(74) *Attorney, Agent, or Firm* — Julie M. Lake; Sheldon O. Heber

(57) ABSTRACT

The present invention relates also to a process for the preparation of intermediate compounds useful in preparing the compounds of Formula (I) using the process of Scheme (II).

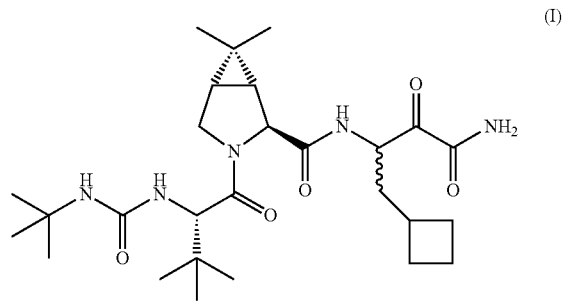

13 Claims, No Drawings

PROCESS FOR PREPARING (1R,2S,5S)-N-[(1S)-3-AMINO-1-(CYCLOBUTYLMETHYL)-2,3-DIOXOPROPYL]-3-[(2S)-2-[[[(1,1-DIMETHYLETHYL)AMINO]-CARBONYL]AMINO]-3,3-DIMETHYL-1-OXOBUTYL]-6,6-DIMETHYL-3-AZABICYCLO[3.1.0]HEXANE-2-CARBOXAMIDE

CROSS-REFERENCE TO RELATED APPLICATIONS

This application is entered into national stage examination under 35 U.S.C. 371 and stems from International patent application no. PCT/US2007/025804 filed in the U.S. PCT receiving office on Dec. 18, 2007, which claims the priority of U.S. provisional patent application Ser. No. 60/876,447 filed Dec. 20, 2006. Each of the aforementioned PCT and Provisional applications is incorporated by reference in its entirety as if fully set forth herein.

FIELD OF THE INVENTION

The present invention relates to a process for the preparation of the compounds of Formula I which have been shown to have activity as HCV protease inhibitors. The present invention relates also to a process for the preparation of intermediate compounds useful in preparing the compounds of Formula I.

FORMULA I

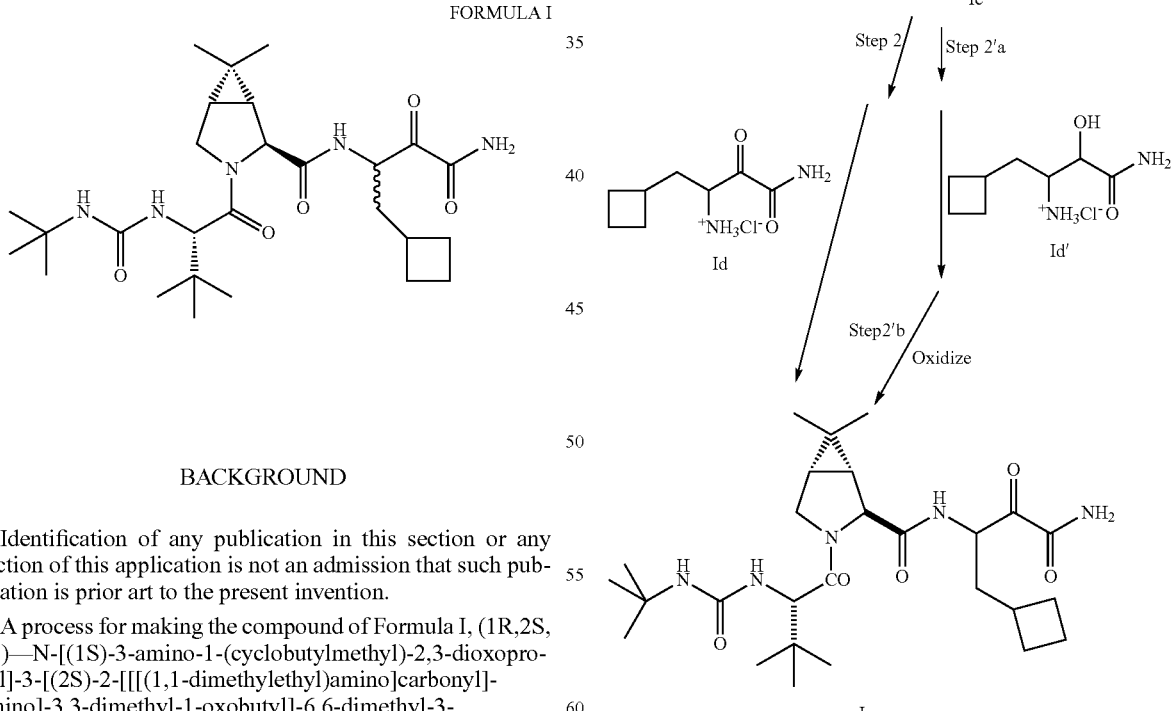

BACKGROUND

Identification of any publication in this section or any section of this application is not an admission that such publication is prior art to the present invention.

A process for making the compound of Formula I, (1R,2S,5S)—N-[(1S)-3-amino-1-(cyclobutylmethyl)-2,3-dioxopropyl]-3-[(2S)-2-[[[(1,1-dimethylethyl)amino]carbonyl]-amino]-3,3-dimethyl-1-oxobutyl]-6,6-dimethyl-3-azabicyclo[3.1.0]hexane-2-carboxamide is described in U.S. Pat. No. 7,012,066 (the '066 patent), Example XXIV, beginning at Column 448 therein. Additional processes for the preparation of the compounds of Formula I are described in published U.S. patent application nos. 2005/0249702, published Nov. 10, 2005, and 2005/0059800, published Mar. 17, 2005.

In general, the process for the preparation of compounds of Formula I is illustrated in Scheme I:

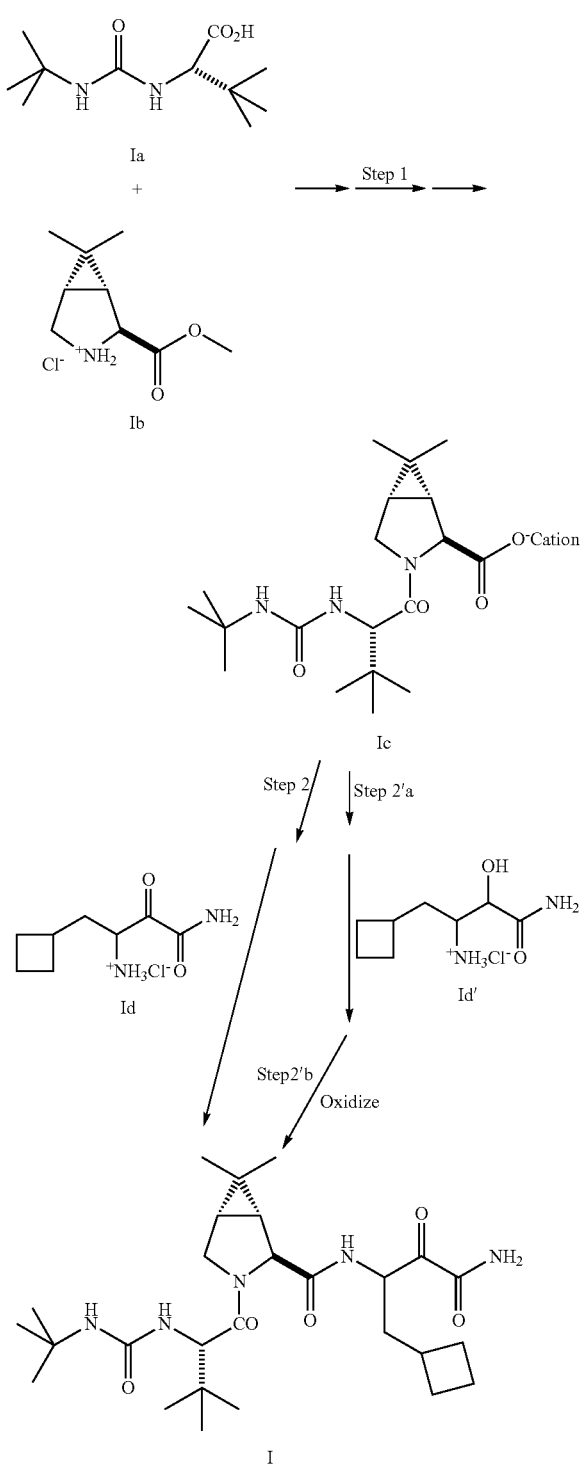

SCHEME I

In accordance with Scheme I, compounds of formula I have been prepared by coupling the compound of Formula Ia with the compound of Formula Ib, preferably, as illustrated in published U.S. application no. 2005/0059800, by treating an acetonitrile solution of 2,6 lutidine and the compound of Formula Ia with an acetonitrile solution containing the compound of Formula Ib, ethyl[(3-dimethylamino)propyl]carbodiimide hydrochloride salt (EDCI-HCl), and 1-hydroxybenzotriazole hydrate (HOBt). After the coupling reaction is complete the reaction mixture provided by Step 1 is worked up by adding methyl-tertiarybutyl ether (MTBE), adjusting the pH with HCl, extracting with sodium bicarbonate and concentrating the organic solution. The concentrate is then diluted with acetonitrile and reconcentrated, then treated with aqueous lithium hydroxide followed by an HCl/isopropyl acetate solution to liberate the free acid, and finally treated with L-α-methylbenzylamine to precipitate the 1c salt form of the coupled product, wherein "salt" is the counter ion of Formula 1f (L-α-methylbenzylamine).

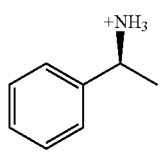

Formula 1f

As illustrated in Scheme I, the compound of Formula I is provided from the compound of Formula Ic using one of two processes. In one process, shown in Steps 2'a and 2' b, a three step procedure, the free acid is generated from the compound of Formula Ic (by treatment with acid, subsequently removing the L-α-methylbenxylamine counterion). The free acid form of Ic is coupled with amine Id' followed by oxidation of the coupled product.

In an alternative process, shown in Scheme I as Step 2, the free acid form of compound Ic is coupled with the amine Id to provide the compound of Formula I directly. Accordingly, with reference to the '066 patent, the coupling process of Step 2 can carried out by treating a DMF/CH$_2$Cl$_2$ solution of the free acid form of compound Ic with amine Id' in the presence of EDCI, HOBt, and N-methylmorpholine to provide the coupled product. After the coupling reaction is complete, the reaction mixture is concentrated, treated with aqueous HCl and the aqueous layer is extracted with dichloromethane. The dichloromethane extract is washed in turn with aqueous NaHCO$_3$, aqueous HCl, and brine, dried with MgSO$_4$, and dried to a solid under vacuum. The alcohol functional group of the coupled product is then oxidized to provide the compound of Formula I. Oxidation can be carried out by treatment with EDCI in mixed toluene/DMSO in the presence of dichloroacetic acid.

In accordance with the foregoing, the previous processes for the preparation of the compound of Formula I using Scheme I requires the use of 1-hydroxy benzotriazole in the first amidation reaction coupling the compounds of formula Ia and Ib to form the intermediate compound of formula Ic. Since HOBt is classified as a reactive solid, and therefor storage and transport of the material is regulated, its use in commercial scale manufacture entails difficulties in handling and storage, and therefore it is desirable to minimize the number of steps in which it is employed. Moreover, when generating the free acid form of the compound of Formula Ic, a solvent distillation step and/or a solvent swap step is needed to improve reaction efficiency, either of which increases free acid degradation. Additionally, the process of Scheme I utilizes the formation of α-methylbenzylamine salts to provide the intermediate Ic in sufficiently pure form that it can be used in the subsequent process step, however, the L-α-methylbenzylamine counterion has been found to react with the isolation solvent, for example, isopropylacetate, to form an N-acetyl-α-methylbenzylamine impurity. Furthermore, the L-α-methylbenzylamine counterion has been found to compete with the amines of Formulae Id and Id' in the subsequent coupling reaction, and to form undesirable byproducts under the reaction conditions of interest. Thus, when the salt intermediate is converted to the free acid, the amine must be separated from the free acid prior to carrying out the second coupling reaction when such processing schemes are employed.

What is needed is a process for providing the compound of Formula I which minimizes the use of HOBT and which obviates the need to regenerate the free acid form of intermediate compound Ic to carry out the second coupling step (Step 2) illustrated in Scheme I.

SUMMARY OF THE INVENTION

In one aspect the present invention is a process for the provision of a compound of Formula I

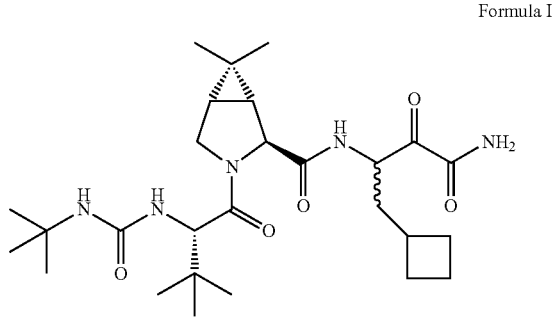

Formula I said process comprising: (i) coupling a tertiaryamine salt of the compound of Formula Ic

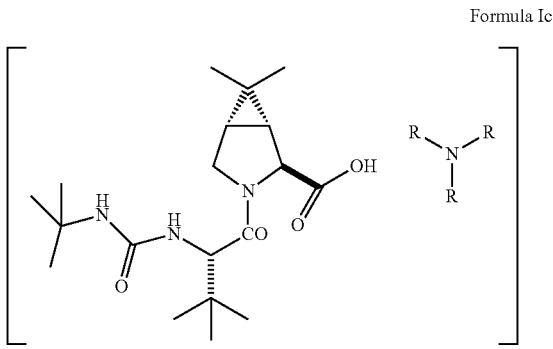

Formula Ic with a salt compound of Formulae Id or Id',

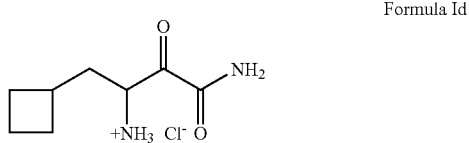

Formula Id

Formula Id'

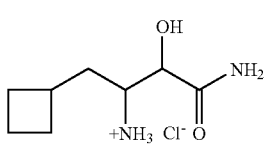

in the presence of at least one coupling reagent and at least one added moiety bearing a basic nitrogen atom selected from a tertiary amine, a tertiary amide, a morpholine compound, and mixtures of two or more thereof; and (ii) when the compound of Formula Id selected in Step (i) is a compound of Formula Id', oxidizing the compound produced in coupling Step (i) to yield the compound of Formula I.

In some embodiments it is preferred to use a non-protic, polar organic solvent in which to carry out the coupling reaction. In some embodiments of the invention it is preferred to prepare run the coupling reaction with a coupling reagent in a medium selected from ethyl acetate, N-methyl-2-pyrrolidinone (NMP), dimethyl formamide (DMF) and mixtures of two or more thereof, more preferably the coupling reaction solvent is ethylacetate in combination with a solvent selected from dimethylformamide (DMF) and N-methyl-2-pyrrolidinone (NMP). In some embodiments it is preferred to use dimethylcylcohexylamine as the counterion in the tertiary amine salt of the compound of Formula Ic, thereby providing a compound of Formula Ic'.

Formula Ic'

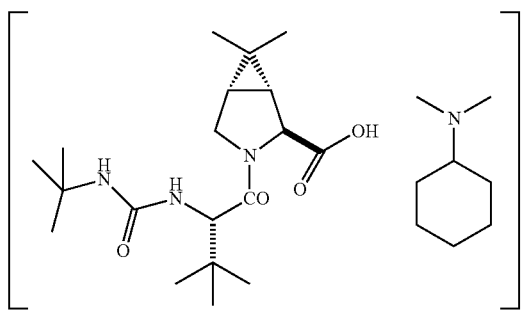

In some embodiments of the invention it is preferred to carry out the reaction using a peptide coupling reagent comprising at least one moiety selected from ethyl(3-dimethylaminopropyl)-carbodiimide-HCl (EDCI-HCl), carbonyldiimidazole (CDI), and 1-chloro-3,5-dimethoxytriazine (DMT-Cl), optionally in conjunction with one or more reagents selected from 1-hydroxybenzotriazole (HOBt), dimethylaminopyridine (DMAP), and 2-hydroxypyridine.

In some embodiments of the invention it is preferred to carry out the coupling reaction in the presence of an added tertiary amine, more preferably a tertiary amine selected from diisopropylethylamine (DIPEA), triethylamine (TEA), 2,6-lutidine, N-methylmorpholine (NMM) and tetraethylenediamine.

In some embodiments of the invention it is preferred to use a coupling reagent selected from coupling reagents, comprising: (i) HOBt-monohydrate in combination with EDCI-HCl; (ii) water wet HOBt in N-methylpyrrolidinone in combination with EDCI-HCl; (iii) DMAP in combination with EDCI-HCl; (iv) carbonyldiimidazole (CDI) in DMF; (v) 1-chloro-3,5-dimethoxy-triazine; (vi) triazine, for example, but not limited to, 1,3,5 trimethoxy-2,4,6-triazine and 2-hydroxypyridine in combination with EDCI-HCl. In some embodiments it is preferred to add a tertirary amine selected from N-methylmorpholine and diisopropylethylamine.

In some embodiments of the invention the process of the invention further comprises a method of forming the compound of Formula Ic, the method comprising:
(a) treating a compound of Formula Ia Formula Ia

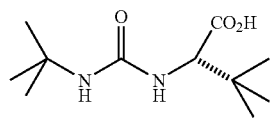

with a compound of Formula Ib

Formula Ib

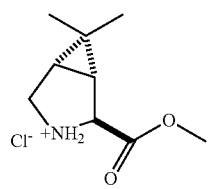

in the presence of EDCI-HCl and 2,6-lutidine and a non-polar, aprotic solvent suitable to provide conditions to form the coupled amide-ester product of Formula Ica, for example, but not limited to, dimethyl formamide (DMF), N-methyl-2-pyrrolidone (NMP), acetonitrile (ACN) or in a mixed solvent comprising acetonitrile and MTBE or EtOAC;

Formula Ica

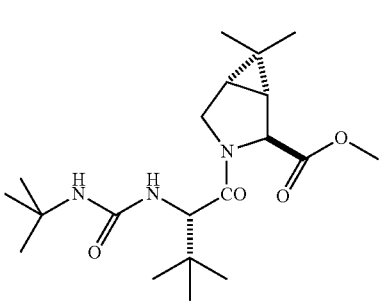

(b) working up the reaction product by sequential treatment with aqueous LiOH followed by HCl and isopropyl acetate to liberate the free acid from the lithium carboxylate form of the product; and (c) treating the free acid with a tertiary amine in a solvent selected from isopropyl acetate, heptanes, heptane, and mixtures of two or more thereof, to precipitate the tertiary amine salt of Formula Ic.

In some embodiments it is preferred to use acetonitrile as the solvent for step "a". In some embodiments it is preferred to use N,N-dimethyl-N-cyclohexylamine as the tertiary amine in Step "c".

In some embodiments it is preferred to use a form of the compound of Formula Ib that comprises the (1R, 2S, 5S) enantiomer in at least about 90% ee, more preferably comprises the (1R, 2S, 5S) enantiomer in at least about 95% ee, more preferably comprises the (1R, 2S, 5S) enantiomer in at least about 98% ee, which ee is retained in the coupling reaction to provide a compound of Formula Ic reflecting the same diastereomeric excess. In some embodiments it is preferred to use a form of the compound of Formula Ib wherein at least about 90% of the amount of the compound of Formula Ib comprises a mixture of two enantiomers, the (1R,2S, 5S) enantiomer and the (1S, 2R, 5R) enantiomer, which composition of isomers is retained in the process of preparing the compound of Formula Ic. In some embodiments it is preferred to employ a mixture in which at least about 95% of the amount of the compound of Formula Ib provided comprises a mixture of the (1S, 2R, 5R) enantiomer and the (1R, 2S, 5S) enantiomer in the process for the formation of the compound of Formula 1c, more preferably at least about 99% of the amount of the compound of Formula Ib provided comprises a mixture of the (1R, 2S, 5S) enantiomer and the (1S, 2R, 5R) enantiomer in the process for formation of the compound of Formula 1c.

Another aspect of the present invention is the provision of the compound of Formula Ic'.

formula Ic'

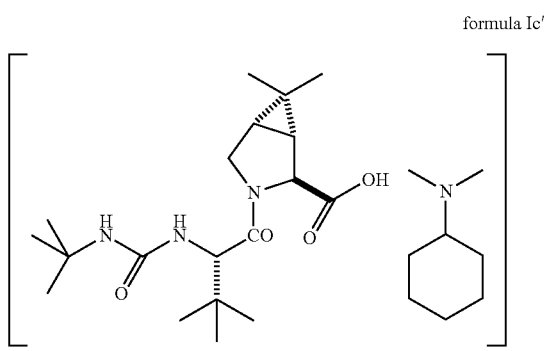

DETAILED DESCRIPTION

As used above, and throughout the specification, the following terms, unless otherwise indicated, shall be understood to have the following meanings:

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and C(O)O-alkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Heterocycl" means a cyclic ring system which contains one or more N, S, or O atoms as a member of the ring structure in combination with up to 10 carbon atoms.

The following abbreviations are used in the description and examples below: RT (room temperature); TEA (triethylamine); CDI (carbonyldiimidazole); DIPEA (diisopropylethylamine); DMAP (N,N-dimethylaminopyridine); DMF (dimethyl-formamide); DMT-Cl (1-chloro-3,5-dimethoxy-triazine), EDCI (ethyl[(3-dimethylamino)propyl]carbodiimide); EtOAc (ethyl acetate); HOBt (1-hydroxy-benzotriazole); IPA (isopropyl alcohol); NMM (N-methylmorpholine); NMP (N-methyl-2-pyrrolidi none); Ac (acetyl); Et (ethyl); THF (tetrahydrofuran); eq (equivalent(s)); MTBE (tert-butylmethylether); Boc (t-butoxy carbonyl).

As mentioned above, the compounds of Formula I have useful activity as HCV protease inhibitors. The inventors have surprisingly found that compounds of Formula I can be prepared in accordance with Scheme II, below, wherein the "R" groups of the amine used in Step Ic are selected from alkyl, substituted alkyl, cycloalkyl and alkylcycloalkyl, and substituted cycloalkyl moieties of from 1 to about 20 carbon atoms.

SCHEME II

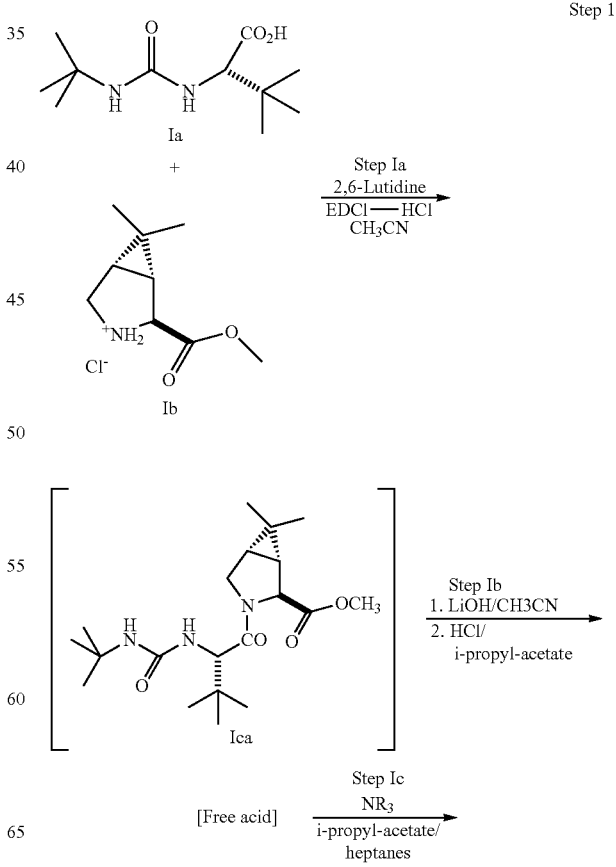

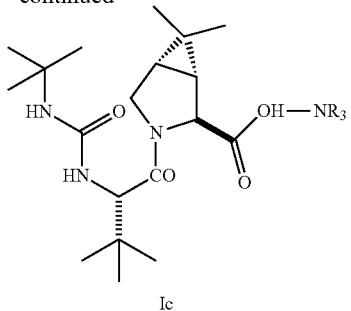

Ic

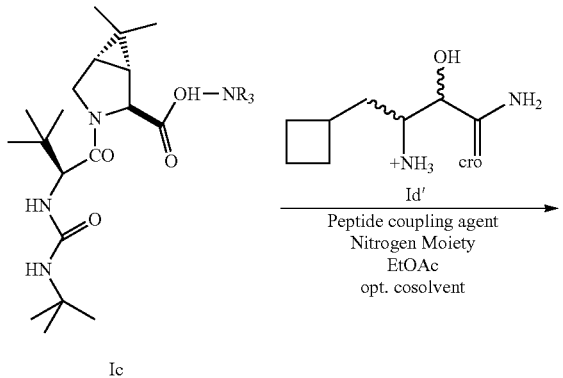

Ic

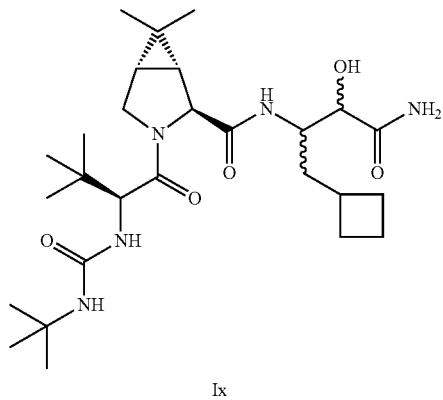

Ix

With reference to Scheme II, surprisingly, in comparison to previous processes, facile, high yield amidation coupling occurs in Step 1 of the process of the invention, coupling 2-tertiarybutyl-ureido-3,3-dimethyl-butyric acid (the compound of Formula (Ia)) to the azabicyclo compound of Formula (Ib)), in an amidation carried out without using 1-hydroxybenzo-triazole (HOBt) to mediate the coupling reaction. Moreover, by carrying out Step 1 in acetonitrile (ACN) or in a mixed solvent comprising acetonitrile and MTBE or EtOAC. Preferably ACN is used in an amount of from about 3× to about 8×V/w relative to the starting material. Step 1 of Scheme II utilizes a tertiary amine to precipitate a salt form of the compound of Formula (Ic), that can be employed directly in the subsequent coupling step without first regenerating the free acid and removing the counter ion moiety used to prepare the salt, as is necessary in previous processes, for example, those processes using L-α-methylbenzylamine. This results in a more efficient process and better utilization of later stage intermediate reagents in the multi-step preparation of compounds of Formula I.

As will be appreciated, the compound of Formula Ib can have four stereoisomers, the (1S, 2R, 5R) stereoisomer (shown in Scheme III as compound Ib-L), the (1R, 2R, 5S) stereoisomer (not shown), the (1S, 2S, 5R) stereoisomer (not shown) and the (1R, 2S, 5S) stereoisomer (shown in Scheme III as compound Ib-D). In some embodiments it is preferred to use in Step I the compound of Formula Ib in a form in which more than 90%, for example more than 98%, of the amount of the isomers present comprise a mixture of the (1S, 2R, 5R) stereoisomer and the (1R, 2S, 5S) stereoisomer, wherein the two enantiomers are present in equal amounts. In some embodiments it is preferred to use in step I the compound of Formula Ib in a form in which one stereoisomer, the (1R, 2S, 5S) isomer (Formula Ib-D), is present in high enantiomeric excess, for example greater than about 90% ee, preferably at least about 95% ee, more preferably at least about 98% ee. Enantiomeric excess ("e.e.") is a percentage expressing the extent to which one enantiomer (e.g., R-enantiomer) is present over the others (e.g. S-enantiomer), calculated by subtracting the difference in the amount of each enantiomer present divided by the sum of the amount of each enantiomer present. Using a form of the compound of Formula Ib that is selected for the desired mixture of enantiomers permits control of the relative amount of the isomers present in the coupled product from the reaction.

The above-mentioned U.S. Pat. No. 7,012,066, and U.S. patent application publication nos. 2005/0249702, published Nov. 10, 2005, 2005/0059800, published Mar. 17, 2005, 2005/0059648 published Mar. 17, 2005 along with a copending application based on and claiming the priority of U.S. provisional patent application Ser. No. 60/753,215 filed Dec. 22, 2005, each of which is incorporated by reference herein in their entirety, describe how to provide the compound of Formula Ib in a form containing the desired mixture of isomers or enrichment in one particular isomer.

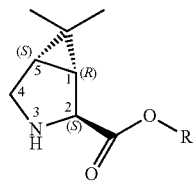

(Ib-D)

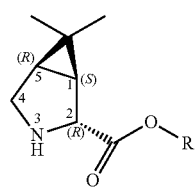

(Ib-L)

Step II of the inventive process, the second coupling step, carries out coupling of the intermediate quarternary amine salt product produced in Step I of the inventive process, for example, the compound of Formula Ic, with, for example, the compounds of Formulae Id and Id', preferably the compound of Formula Id'. The inventors have found that the use of mixed ethyl acetate and DMF or ethylacetate and NMP as a solvent system in which the coupling is carried out, and the selection of a tertiary amine as the counter ion in the salt form of the reagent in this second step permits the present invention process to utilize the salt compound directly in the reaction rather than needing to first regenerate the free acid form of product (Ic), as was required in the prior processes mentioned above. Step 2 of the process of the present invention is carried out in the presence of at least one additional moiety bearing a basic nitrogen atom and at least one peptide coupling reagent.

Selected conditions of the inventive process provide reduced impurities in the product of Formula I.

Although it is advantageous to use both Steps I and II of the present process together, it will be appreciated that some of the advantages offered by each of the individual steps can be realized when practiced individually and integrated into published methods. Each of these processing steps is discussed next in greater detail.

Step I—First Amidation Coupling Reaction.

The first step involves coupling the azabicyclo compound of Formula (Ib) with the acid compound of Formula (Ia). The coupling reaction is carried out in the presence of one or more 2,6-substituted pyridine compounds, for example, 2,6-lutidine, and a coupling reagent, for example, the hydrochloride salt of (ethyl[(3-dimethylamino)propyl]carbodiimide) (Formula Ia1).

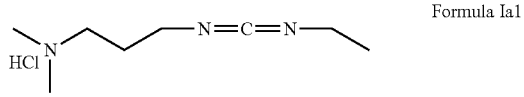

Formula Ia1

Suitable solvents for carrying out the reaction are polar, aprotic, organic solvents, for example, acetonitrile and ethyl acetate (EtOAC). Preferably the reaction is carried out at a temperature of from about 5° C. to about 30° C. In general, the reaction is run using one equivalent of the compound of formula Ia and an amount of the compound of Formula Ib which is from about 0.9 equivalents to about 1.1 equivalents in comparison to the amount of the compound of Formula Ia employed. In general, the reaction will use one or more pyridine base in an amount of from about 0.5 eq. to about 2.5 eq. relative to the amount of the compound of Formula Ia employed, and one or more coupling agents in an amount of at least 1.05 equivalents relative to the amount of the compound of Formula Ia employed. In general, the reaction will be run for four hours to insure complete coupling of the starting materials. Typically the reaction will be followed by LC and considered completed when less than about 0.75% of the starting compound of Formula Ia remains in the reaction mixture.

Although it is preferred to employ EDCI as a coupling agent in the reaction, other coupling agents may be used instead of EDCI or in addition to EDCI, for example pivaloyl chloride, propane phosphonic acid anhydride and mixed (EDCI/DMAP). It is preferred to employ 2,6-lutidiene as a substituted pyridine base, but it will be appreciated that other pyridine bases, for example, other 2,6 alkyl-substituted pyridines, triethyl amine, and NMM can also be employed instead of 2,6-lutidine or in addition to 2,6-lutidine.

After the coupling reaction has run to completion, the reaction mixture is worked up by adding methyl tert-butyl ether to the reaction mixture, and washing the resultant mixture with HCl aqueous solution followed by sodium bicarbonate solution, then concentrating the organic layer to 3× (that is, to about ⅓ of its initial volume), which, after concentration, contains primarily acetonitrile. The reaction mixture is subsequently treated with a metal hydroxide base in water, followed by HCl or another suitable acid, for example, $H_2SO_4$, followed by a solvent selected from isopropyl acetate and 2-methyltetrahydrofuran (Me-THF), thereby liberating the free acid form of the product of Formula Ic.

After liberation of the free acid form of the compound of Formula Ic, the reaction mixture is treated with a tertiary amine to precipitate an ammonium salt form of the compound of Formula Ic. As shown in Scheme II, the tertiary amine interacts with the free acid functionality of the compound forming a counter ion in the salt. In some embodiments it is preferred to use a single component solvent, preferably isopropyl acetate. In some embodiments it is preferred to include an antisolvent mixed with the solvent in which the tertiary amine is dissolved, for example, isopropyl acetate/heptanes. In these embodiments, mixture of the reaction mixture with the tertiary amine solution results in precipitation of a salt form of a compound of Formula 1c, which can be collected by filtration and dried for use in Step 2. In some embodiments it is preferred to use N,N-dimethyl-N-cyclohexyl amine as the tertiary amine for precipitating the coupled product.

Step II—Second Amidation Coupling Reaction.

The second step of the process of the invention for preparing the compound of Formula I is to carry out a second coupling reaction between the ammonium salt compound Ic provided by the Step I and a salt compound selected from the compound of Formula Id and the compound of Formula Id'. In some embodiments of the invention it is preferable to utilize the compound of Formula Id'. Accordingly, the second amidation coupling reaction is carried out by reacting the compound of Formula Ic with the selected salt compound of Formula Id in the presence of at least one peptide coupling reagent and one or more reagents containing a basic nitrogen atom selected from a tertiary amine, an amide, and a morpholine compound and mixtures of two or more thereof. Generally the reaction is carried out at a temperature of from about −10° C. to about +30° C., preferably less than about 30° C.

In some embodiments it is preferred to use ethyl acetate as the solvent. Other solvents which may be used include dimethylformamide (DMF), N-methylpyrrolidinone (NMP), dimethylacetamide, and acetonitrile (ACN), and mixtures of two or more thereof. Suitable peptide coupling reagents for use in the present invention process Step II include, but are not limited to, for example, 1-hydroxy-benzotriazole (HOBt, both water wet and hydrate), ethyl[(3-dimethylamino)propyl]carbodiimide-hydrochloride (EDCI-HCl), carbonyldiimidazole (CDI), 1-chloro-3,5-dimethoxytriazine (DMT-Cl), 2-hydroxypyridine, and combinations of two or more thereof. In some embodiments of the present invention it is preferred to utilize the selected coupling agent(s) in a solvent selected from ethyl acetate, dimethyl formamide (DMF), N-methyl-2-pyrrolidone (NMP), and combinations of two or more thereof. In some embodiments of the present invention it is preferred to utilize one or more moieties containing a basic nitrogen atom selected from triethylamine, diisopropylethylamine, 2,6,-lutidine, N-methylmorpholine, and tetramethylethylene diamine.

In some embodiments of the invention it is preferred to use a coupling reagent comprising one or more coupling agents and a solvent selected from the following combinations: (i) HOBt-monohydrate in ethyl acetate with DMF or NMP in combination with EDCI-HCl; (ii) water wet HOBt in ethylacetate with N-methylpyrrolidinone in combination with EDCI-HCl; (iii) DMAP in ethylacetate with DMF or N-methylpyrrolidinone (NMP) in combination with EDCI-HCl; (iv) carbonyldiimidazole (CDI) in ethylacetate and DMF; (v) 1-chloro-3,5-dimethoxy-triazine in ethylacetate with DMF; (vi) 1,3,5 trimethoxy-2,4,6-triazine; and (vii) 2-hydroxypyridine in ethyl acetate with DMF with EDCI-HCl. In some embodiments it is preferred to add the tertiary amine diisopropylethylamine or N-methyl morpholine as a moiety having a basic nitrogen atom.

In general the ratio of the amount of ammonium salt of Formula Ic to the amount of salt compound of Formula Id used with be from about 0.76 equivalents of ammonium salt Ic: 1.0 equivalent of the salt compound of Formula Id to about 1.0 equivalent ammonium salt Ic:1.1 equivalent salt compound of Formula Id, preferably a ratio of 1:1.1 will be employed. In general, the amount of coupling agent used will be at least about 1.05 equivalents, based on the amount of ammonium salt of Formula Ic employed. In general the amount of added tertiary amine provided with be from about 0.5 equivalents to about 2.5 equivalents, preferably from about 0.75 equivalents to about 2.0 equivalents based on the amount of the compound of Formula Ic present.

In those embodiments in which the salt compound of Formula Id' was employed, with reference to Scheme I, above, a second step (2' b) is carried out in which the —OH functional group of the adduct is oxidized to provide the corresponding ketone, thus providing the compound of Formula I. This oxidation can be carried out in accordance with procedures in the above-mentioned patents and published applications, for example, the procedure described in U.S. Pat. No. 7,012,066 at column 451, lines 20 to 29, and the procedure described in copending U.S. application Ser. No. 60/736,542 filed Nov. 14, 2005.

The starting materials used in Step I of the present process, and the salt compounds of Formula Id used in Step II of the present process can be prepared in accordance with procedures described in any of the above-mentioned patents and published applications.

EXAMPLES

Example I

Preparation of Ic' (N,N-dimethylcyclohexyl amine Salt) According to Scheme II, Step I Into a reactor (R-1) was charged 351 kg of compound Ia, 314 kg of compound Ib, and 807 L of acetonitrile. Batch temperature was adjusted to 0 to 10° C. 323 kg of 2,6-lutidine followed by 123 L of acetonitrile was charged to R-1, while maintaining temperature at 0 to 15° C. 351 kg of EDCI-HCl followed by 123 L of acetonitrile was charged to between 5 to 25° C. The mixture was stirred at 20 to 30° C. for 4 h. Reaction completion was checked by HPLC to show less than 0.75% of un-reacted compound Ia. 1755 L of MTBE followed by 807 kg of 9.9% HCl was charged to R-1 between 15° C. to 25° C. The batch was stirred for 15 minutes and settled for at least 30 minutes, and the aqueous layer was split to HOLD TANK. 807 kg of 9.9% HCl was charged to R-1 at 15 to 25° C. The batch was stirred for 15 minutes and settled for 30 minutes, and the aqueous layer was split to HOLD TANK. 211 kg of sodium bicarbonate followed by 4001 L of water was charged to R-2, and the whole was agitated until all solid dissolved. 1404 L of the NaHCO₃ solution in R-2 was transferred to R-1 at 15 to 25° C. The mixture was stirred for 15 minutes and settled for at least 30 minutes. The aqueous layer was split to HOLD TANK. 140 kg of sodium chloride was charged to the NaHCO₃ solution in R-2. Half of the NaHCO₃/NaCl solution in R-2 was transferred to R-1. The whole in R-1 was agitated for 15 minutes and settles for at lest 30 minutes. The aqueous layer was split to HOLD TANK. The remainder of the NaHCO₃/NaCl solution in R-2 was transferred to R-1. The whole in R-1 was agitated for 15 minutes and settled for at lest 30 minutes. The aqueous layer was split to HOLD TANK. The batch in R-1 was concentrated to about 1053 L under vacuum. 97 kg of lithium hydroxide Monohydrate followed by 1404 L of water was charged to R-2, and the mixture was stirred at 20 to 30° C. until all solids dissolved. The lithium hydroxide solution in R-2 was transferred to R-1. The whole was stirred at 20 to 30° C. for 3 h. Hydrolysis completion was checked by HPLC to show 100% conversion. 1053 L of MTBE followed by 1404 L of water was charged to R-1. The mixture was stirred for 20 minutes and settles for at least 30 minutes. The aqueous layer was split to R-2. The organic layer was transferred to HOLD TANK. 1053 L of MTBE was charged to R-2. The mixture was stirred for about 10 minutes and settled for at least 30 minutes. The aqueous layer was transferred to R-1. The organic layer was transferred to HOLD TANK. 293 kg of 9.9% HCl followed by 1530 kg of isopropyl acetate and 660 kg of 9.9% HCl was charged to R-1 at 20 to 30° C. The mixture in R-1 was stirred for 30 minutes and settled for at least 30 minutes. The aqueous layer was split to HOLD TANK. 35 kg of Sodium Chloride followed by 702 L of water was charged to R-2. The NaCl solution in R-2 was transferred to R-1. The mixture was stirred for 15 minutes at 15 to 25° C. and settled for at least 30 minutes. The aqueous layer was split to HOLD TANK. The batch in R-1 followed by 306 kg of isopropyl acetate rinse was transferred to R-2 via 1 µm inline filter. The batch in R-2 was concentrated to about 1404 L under vacuum at 35 to 60° C. 918 kg of isopropyl acetate was charged to R-2, and the batch was concentrated to about 1404 L under vacuum at 35 to 60° C. Water content in the batch was <0.5% w/w. 1530 kg of isopropyl acetate was charged to R-2. The batch temperature was adjusted to 43 to 48° C., and 109 kg of N,N-dimethylcyclohexylamine (DMCA) was charged to R-2. 4 kg of compound Ic' seed in 11 L of isopropyl acetate was charged to R-2. The batch was stirred for 5 h at 43 to 48° C. for 1 h. 130 kg of DMCA was charged to R-2 over 2 h at 43 to 48° C. 153 kg of isopropyl acetate rinse was charged to R-2. The batch was cooled to 5 to 10° C. over a period of 3 hours. The batch was filtered in portions with a centrifuge. The wet cake was washed with cold isopropyl acetate and was dried under vacuum at 25° C. for 4 h followed by at 45° C. for at least 8 h. 706 kg of Compound Ic' was obtained (90% yield). ¹H NMR (DMSO-d₆), δ 0.80 (s, 3H), 0.91 (s, 9H), 0.99 (s, 3H), 1.02-1.25 (m, 5H), 1.17 (s, 9H), 1.35 (d, J=8 Hz, 1H), 1.43 (dd, J=5 and 8 Hz, 1H), 1.54-1.58 (m, 1H), 1.68-1.78 (m, 3H), 2.23 (s, 6H), 2.28 (m, 1H), 3.73 (dd, J=5 and 10 Hz, 1H), 3.96 (d, J=10 Hz, 1H), 4.08 (s, 1H), 4.15 (d, J=10 Hz, 1H), 5.87 (d, J=10 Hz, 1H), 5.95 (brs, 1H).

Example 2

Preparation of the Compound of Formula Ix According to Scheme II, Step 2 Using Wet HOBT in NMP with EDCI-HCl Present Into a reactor was charged 80 mL of ethylacetate to a reactor followed by 20.01 g (40.4 mmol) of Ic', and 9.20 g (44.1 mmol, 1.09 equivalents) of Id'. An additional 20 mL of ethyl acetate and 20.5 g N-methylpyrrolidinone was charged into the reactor. The reactor contents were cooled to 15° C. Additionally 3.67 g (27.16 mmol, 0.59 equivalents) of 1-hydroxybenzotriazole monohydrate followed by 2.96 g of water were charged. N-methylmorpholine (2.83 g, 28.0 mmol, 0.63 equivalents) and subsequently ethyl[(3-dimethylamino)propyl]carbodiimide-hydrochloride (EDCI-HCl), (9.98 g, 52.1 mmol, 1.30 equivalents) were sequentially charged into the reaction mixture. The reaction mixture was stirred at 15° C. until complete (<0.5 area % Ic' remaining by LC analysis), in this case 3 h.

The reactor temperature was increased to 20° C. and 80 mL of DI water followed by 40 mL of 9.9% aqueous hydrochloric acid was added. The reactor was stirred at 20° C. for 13 minutes then allow to split for 90 minutes. The aqueous layer was removed and treated with 60 mL of ethyl acetate. This mixture was stirred at 20° C. for 20 min then allowed to split for 25 minutes. The organic layer was combined with the previous organic layer. The combined organic layers were treated with 80 mL DI water and 40 mL 9.9% aqueous hydrochloric acid. The mixture was stirred at 20° C. for 15 minutes then allowed to split for 28 minutes. The aqueous layer was removed to waste. The organic layer was treated with 120 mL of 0.45M potassium carbonate solution and stirred at 20° C. for 21 minutes then allowed to split for 30 minutes. This aqueous layer was removed to waste. The organic layer was then treated with 120 mL of 0.45M potassium carbonate solution and stirred at 20° C. for 31 minutes then allowed to split for 28 minutes with subsequent removal of the aqueous layer to waste. The organic layer was treated with 120 mL of DI water and stirred at 20° C. for 15 minutes then the layers were allowed to split for 59 minutes. The aqueous layer was removed to waste. Solution yield by LC of the compound of Formula Ix in organic layer is 92%.

Example 2a

On a similar batch with 100 g starting Ic' the organic layer obtained containing the compound of Formula Ix was then concentrated to 486.45 g. 162.17 g of this material (KF=5.6%) was treated with 92 mL of ethyl acetate and concentrated by rotary evaporation to 98 mL then treated with 7 mL ethyl acetate (KF=3.0%). 0.75 mL of DI water was added to bring the KF to 3.8%. This ethyl acetate solution was added slowly by syringe pump over 2 h to −10° C. heptanes in a round bottom flask. Following the addition, the slurry was stirred at −10° C. for 15 minutes then filtered and washed with 66 mL then 55 mL of cold heptanes. The white solid was dried on the filter for 30 minutes then in a room temperature vacuum oven for 3 days. The temperature on the vacuum oven was increased to 70° C. for 1 day. The final solid amount of the compound of Formula was 31.51 g, 89.6% yield.

Example 3

Preparation of the Compound of Formula Ix According to Scheme II, Step 2 Using HOBT Monohydrate with EDCI-HCl Present EDCI-HCl (244.00 kg, 1272 mol, 1.27 equiv), 1-hydroxybenzotriazole hydrate (80.00 kg, 592 mol, 0.59 equiv), and 236.00 kg (1131 mol, 1.13 equiv) of the compound of Formula 1d' (Scheme II, Step 2) were charged to a reactor and dissolved in DMF (1407 kg) and ethyl acetate (1492 L). The reaction was cooled to 6.2° C. and diisopropylethylamine (80.00 kg, 619 mol, 0.62 equiv) was added followed by 525.00 kg of the compound of Formula Id' (94.68% w/w, 1004 mol, 1.00 equiv) as a solid charge. The reaction mixture was maintained at a temperature of from 0° C. to 10° C., with stirring, for 30 min then warmed to 20° C. to 25° C. over 1.5 hour and maintained, at a temperature of 20° C. to 25° C. for 3.5 h with continued stirring. The reaction temperature was adjusted to 15° C. to 25° C. and water (2486.5 L) and ethyl acetate (3486.8 L) were added followed by 36% HCl (224.00 kg). This mixture was agitated for 15 minutes then the aqueous layer was removed. The aqueous layer was back-extracted with ethyl acetate (5438 L). The combined organics were treated with water (1988.5 L) and 36% HCl (70.00 kg). This mixture was agitated for 15 minutes and the aqueous layer was removed. The organic layer was then treated with 0.45 M $K_2CO_3$ (aq) (1991.2 L water and 124.00 kg $K_2CO_3$). This mixture was agitated for 15 minutes and the aqueous layer was removed. The organic layer was treated with 0.75 M $KHCO_3$ (aq) (2010 L). This mixture was agitated for 15 minutes and the aqueous layer was removed. The organic layer was treated with 0.75 M $KHCO_3$ (aq) (1935 L). This mixture was agitated for 15 minutes and the aqueous layer was removed. The organic layer was treated with water (1989.6 L). This mixture was agitated for 15 minutes and the aqueous layer was removed. The organic layer was concentrated under vacuum to 1590 L, water (19.1 L) was added, and the mixture was added to −10° C. heptanes (7457.3 L) over 2.5 h. The resultant solid product was isolated by centrifuge filtration, washed with cold heptanes, and dried under vacuum at 30° C. for 6 h then 70° C. for 15 h to give the compound of Formula Ix as a white solid (473.55 kg, 90.4%).

Example 4

Preparation of the Compound of Formula Ix According to Scheme II, Step 2 Using HOBT with EDCI-HCl Present and Selected Enantiomers of the Compound of Formula 1d'

The compound of Formula 1d' (Scheme II, Step 2) comprising 2.5 g (12 mMol.) of the combined (S,S and R,R) enantiomers and 0.25 g (1.2 mMol.) of the combined (R,S and S,R) enantiomers (enantiomeric pair ratio 87/13, [(RR+SS)/(RS+SR)]) were combined with 1.0 g of 1-hydroxybenzotriazole hydrate (HOBT, 7.4 mmol) in 21 ml of ethyl acetate. This mixture was cooled to a temperature between 0° C. to 5° C. To the reaction mixture was added 2.1 g of N,N-diisopropylethylamine (16.2 mmol), 5 ml of 1-methyl-2-pyrrolidinone, and 4.7 g of the compound of Formula 1c' (9.5 mmol), followed by 2.85 g of 1-(3-dimethylaminopropyl)-3-ethylcarbodiimide hydrochloride (EDCI HCl, 14.9 mmol). The temperature of the reaction mixture was maintained between 0° C. and 10° C. with stirring for 15 min, then slowly warmed to a temperature between 20° C. and 25° C. and maintained in that temperature range with stirring overnight. At the end of the stirring period, 40 mL of ethyl acetate and 25 mL of 3N of HCl where added to the reaction mixture while maintaining the temperature between 15° C. and 25° C. The layers were separated. The organic layer was washed successively with one aliquot of 15 ml of 3N of HCl, one aliquot of 15 ml of water, three aliquots of 20 mL of 10% of potassium carbonate in water, and one 20 mL aliquot of water. The organic layer was concentrated, added ethyl acetate again, and concentrated to dry. The product of Formula Ix was obtained as a white powder (3.3 g, in a ratio of 87/13 of (RR+SS)/(RS+SR).

Example 5

Preparation of the Compound of Formula Ix According to Scheme II, Step 2 Using HOBT with EDCI-HCl Present and Selected Enantiomers of the Compound of Formula 1d'

The compound of Formula 1d' (Scheme II, Step 2) comprising 2.5 g (12 mMol.) of the combined (S,R and R,S) enantiomers and 0.25 g (1.2 mMol.) of the combined (S,S and R,R) enantiomers (enantiomeric pair ratio 10/90, [(RR+SS)/(RS+SR)]) were combined with 1.0 g of 1-hydroxybenzotriazole hydrate (HOBT, 7.4 mmol) in 21 ml of ethyl acetate. This mixture was cooled to a temperature between 0° C. to 5° C. To the reaction mixture was added 1.8 g of N,N-diisopropylethylamine (13.9 mmol), 5 ml of 1-methyl-2-pyrrolidinone, and 4.7 g of the compound of Formula 1c' (9.5 mmol), followed by 2.35 g of 1-(3-dimethylaminopropyl)-3-ethylcarbodiimide hydrochloride (EDCI HCl, 12.2 mmol). The temperature of the reaction mixture was maintained between 0° C. and 10° C. with stirring for 15 min, then slowly warmed to a temperature between 20° C. and 25° C. and maintained in that temperature range with stirring overnight. At the end of the stirring period, 40 mL of ethyl acetate and 25 mL of 3N of HCl where added to the reaction mixture while maintaining the temperature between 15° C. and 25° C. The layers were separated. The organic layer was washed successively with one aliquot of 15 ml of 3N of HCl, one aliquot of 15 ml of water, one aliquot of 20 mL of 10% of potassium carbonate in water, and one 20 mL aliquot of water. The organic layer was concentrated, added ethyl acetate again, and concentrated to dry. The product of Formula Ix was obtained as a white powder (3.8 g, in a ratio of 10/90 of (RR+SS)/(RS+SR).

Example 6

Preparation of the Compound of Formula Ix via Intermediate Prepared from CDI Treatment of the Compound of Formula Ic'

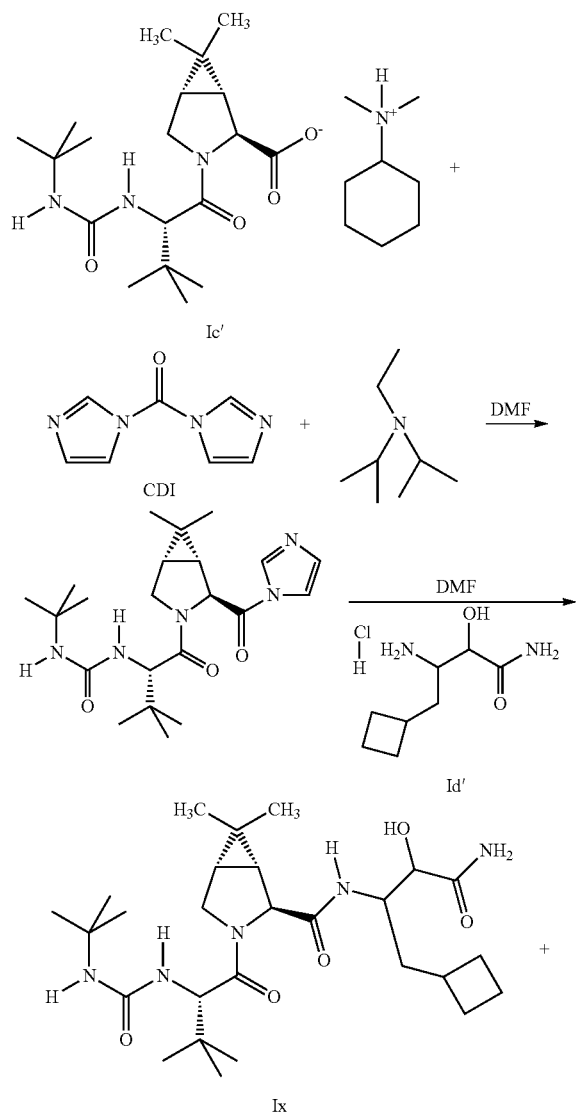

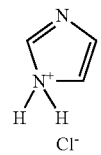

The compound of Formula Ix was produced in coupling reactions using CDI in accordance with the following procedure:

1. Charge 53.2 g 1C' salt (94.3 wt/wt %, 50 g active)
2. Charge 150 ml (3×) DMF (KF: 0.1%);
3. Charge 11-16 ml DIPEA (0.8-1.2 eq., KF: 0.04%) and then 19.2 g (1.15 eq.) CDI;
4. Agitate batch at rt for 2-3 hr
   Note: add more CDI to push reaction to completion if needed;
5. charge 23.75 g (1.12 eq.) 1d' at ambient temperature, agitate at ambient temperature until reaction is completed;
6. cool batch to 10° C. and add 350 ml (7×) EtOAc and then 250 ml (5×) water;
7. adjust pH of the aqueous layer to ~0.5 with concentrated HCl maintaining reaction mixture at 15° C.-20° C. and split layers;
8. wash organic layer with 1N HCl 2-3 times;
9. wash organic layer with two aliquots of 8-10% aqueous $K_2CO_3$ and/or $KHCO_3$ solution;
10. wash organic layer with 4× water
11. assay and/or isolate from organic layer, typically 80.3% solution yield of the compound of Formula IX with 98.95 area 98.95 area % purity Example 7a Preparation of the Compound of Formula Ix According to Scheme II Using 2-Hydroxypyridine as a Coupling Agent in the Presence of EDCI-HCl Into a reaction vessel containing 100 mL of a 1:1 mixture of methyl t-butyl ether and DMF at room temperature were suspended 11.70 g of EDCI-HCl (61.0 mmol, 1.62 equiv), 11.31 g of the compound of Formula Id' (54.2 mmol, 1.44 equiv), and 2.64 g of 2-Hydroxypyridine (27.8 mmol, 0.74 equiv). Diisopropylethylamine (12.8 mL, 73.5 mmol, 1.95 equiv) was added to the reaction mixture followed by a 20.00 g charge of the compound of Formula Ic' in solid form ((93.1% w/w), 37.6 mmol, 1.00 equiv). The reaction mixture was stirred over night at room temperature (19° C. to 22° C.) and monitored by HPLC for completion. At the end of the stirring period, 50 mL of methyl t-butyl ether and 50 mL of 2.5% aqueous HCl were added to the reaction mixture. The aqueous layer was back-extracted with 4 aliquots of 50 mL methyl t-butyl ether. The combined organic layers were washed sequentially with 100 mL 2.5% HCl (aq), 100 mL 1% HCl (aq), 100 mL water, 100 mL 0.45 M $K_2CO_3$ (aq), 100 mL 0.75 M $KHCO_3$ (aq), and 100 mL water. The organic layer was concentrated to 136 mL and cooled to 10° C. To the cold, concentrated organic layer was added 200 mL 0 heptanes over 50 minutes. The resulting slurry was agitated for 50 minutes, and the solids were isolated by filtration and washed with 35 mL heptanes. The solids thus obtained were dried under vacuum at 75° C. overnight to give ~1 g white solid (loss to filtrate and flask walls 4.59 g) of the desired product (total yield 26.6%).

Example 7b

Preparation of the Compound of Formula Ix According to Scheme II Using DMAP as a Coupling Agent in the Presence of EDCI-HCl Into a reaction vessel containing 120 mL of a 1:1 mixture of ethyl acetate and DMF at room temperature were suspended 9.75 g EDCI-HCl (50.9 mmol, 1.35 equiv), 9.79 g of the compound of Formula Id' (46.9 mmol, 1.24 equiv), and 2.76 g DMAP (22.6 mmol, 0.60 equiv). Diisopropylethylamine (10.2 mL, 58.6 mmol, 1.51 equiv) was added to the reaction mixture followed by a 20.03 g charge of the compound of Formula Ic' in solid form ((93.1% w/w), 37.7 mmol, 1.00 equiv). The reaction mixture was stirred for 17 hours at room temperature (19° C. to 22° C.) and monitored by HPLC for completion. When the reaction was complete, 50 mL of ethyl acetate and 100 mL of 2.5% aqueous HCl were added to the reaction mixture. The aqueous layer was back-extracted with 60 mL ethyl acetate. The combined organic layers were washed sequentially with 80 mL 1% HCl (aq), 80 mL water, 80 mL 0.45 M $K_2CO_3$ (aq), 80 mL 0.75 M $KHCO_3$ (aq), 80 mL 0.75 M $KHCO_3$ (aq), and 80 mL water and then concentrated by rotary evaporation to 47.45 g. The SS isomer crystallized from the concentrate and 2.75 ml of water was added to the slurry. The SS isomer dissolved within 4-5 hours. The organic concentrate was added to 171 mL of 0° C. heptanes over 47.5 min. and stirred at 0° C. for 30 min. Solids precipitated from the mixture and the solid product isolated by vacuum filtration. The solids thus obtained were dried at 75° C. in a vacuum oven for 18 h to provide 11.2 g (56.9% yield, 91.0% wt/wt purity) of the compound of Formula Ix.

Example 7c

Preparation of the Compound of Formula Ix According to Scheme II Using 1,3,5-Trimethoxy-2,4,6 Triazine a Coupling Agent in the Presence of EDCI-HCl Into a reaction vessel containing 100 mL of a 1:1 mixture of ethyl acetate and DMF at room temperature were suspended 7.56 g of 1,3,5-trimethoxy-2,4,6-triazine (43.1 mmol, 1.13 equiv) and 9.79 g of the compound of Formula Id' (46.9 mmol, 1.23 equiv). N-Methylmorpholine (4.7 mL, 42.7 mmol, 1.12 equiv) was added to the reaction mixture followed by a 20.01 g charge of the compound of Formula Ic' in solid form ((93.9% w/w), 38.0 mmol, 1.00 equiv). The reaction was stirred for 25.5 hours at room temperature (19° C. to 22° C.) and monitored by HPLC for completion. When the reaction was complete to the reaction mixture was added 50 mL of ethyl acetate and 100 mL of 1M aqueous citric acid. The aqueous layer was back-extracted with 60 mL ethyl acetate. The combined organic layers were washed sequentially with 100 mL 1 M citric acid (aq), 80 mL 1M citric acid (aq), 85 mL water, 80 mL 0.45 M $K_2CO_3$ (aq), 80 mL 0.75 M $KHCO_3$ (aq), 80 mL water, and 80 mL 1M citric acid (aq). HPLC analysis indicated that the solution contained an 84.7% yield of the Compound of Formula 1x.

While the present invention has been described with and in conjunction with the specific embodiments set forth above, these examples are meant to be illustrative and not limiting. Many alternatives, modifications and other variations thereof will be apparent to those of ordinary skill in the art. All such alternatives, modifications and variations are intended to fall within the spirit and scope of the present invention.

The invention claimed is:

1. A process for the provision of a compound of Formula I

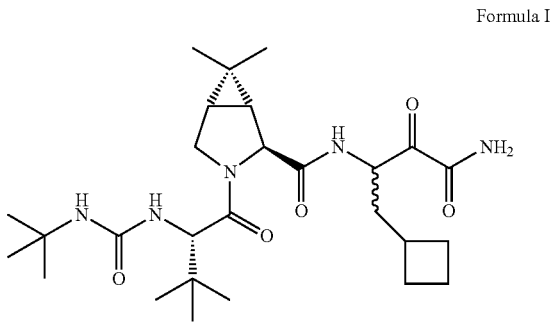

Formula I said process comprising:
(i) coupling a tertiaryamine salt of the compound of Formula Ic Formula Ic with a compound selected from the salt compounds of Formulae Id and Id'

Formula Id

Formula Id' in the presence of at least one peptide coupling reagent and at least one reagent having a basic nitrogen atom selected from a tertiary amine, a tertiary amide, a morpholine compound and mixtures of two or more thereof; and
(ii) when the salt compound selected in Step (i) is a compound of Formula Id', oxidizing the compound Ic produced in Step (i) to yield the compound of Formula I.

2. The process of claim 1 wherein Step (i) is carried out in a polar organic solvent which is ethylacetate, acetonitrile, dimethylformamide, dimethylacetamide, and N-methylpyrrolidinine (NMP), or mixtures of two or more thereof, and wherein the counter ion $R_3N$ in the compound of Formula Ic is N,N-dimethylcyclohexylamine.

3. The process of claim 1 wherein the counter ion R₃N in the compound of Formula Ic is N,N-dimethylcyclohexylamine.

4. The process of claim 3 wherein the peptide coupling reagent is selected from: (i) HOBt-monohydrate in ethyl acetate with dimethyl formamide (DMF) in combination with EDCI-HCl; (ii) HOBt-monohydrate in ethyl acetate with NMP in combination with EDCI-HCl (iii) water wet HOBt in ethyl acetate with N-methylpyrrolidinone (NMP) in combination with EDCI-HCl; (iv) DMAP in ethyl acetate with N-methylpyrrolidinone (NMP) in combination with EDCI-HCl; (v) DMAP in ethyl acetate with DMF in combination with EDCI-HCl (v) carbonyldiimidazole (CDI) in ethyl acetate with DMF; (vi) 1-chloro-3,5-dimethoxy-triazine in ethyl acetate with DMF; (vii) 1,3,5 trimethoxy-2,4,6-triazine in ethyl acetate with DMF; and (viii) 2-hydroxypyridine in an ethyl acetate/DMF mixture in the presence of EDCI-HCl.

5. The process of claim 4 wherein the additional moiety bearing a basic nitrogen added in step (i) is selected from diisopropylethylamine, N-methylmorpholine, triethylamine, 2,6-lutidine, and tetramethylethylenediamine.

6. The process of claim 1 further comprising a process for providing the compound of Formula Ic, said process comprising:

(a) coupling a compound of Formula Ia

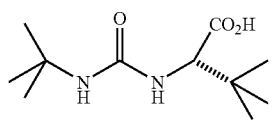

Formula Ia with a compound of Formula Ib

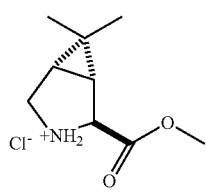

Formula Ib in the presence of EDCI-HCl, 2,6-lutidine, and a solvent suitable to provide conditions to form a reaction mixture containing the coupled amide product of Formula Ica;

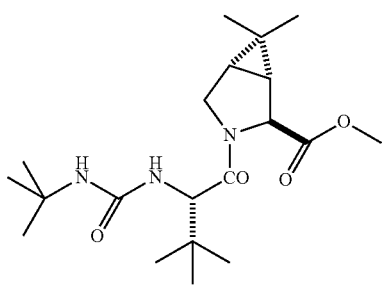

Formula Ica (b) working up the reaction mixture produced in step (a) by sequential treatment of said reaction mixture with LiOH in water followed by HCl in isopropyl acetate to liberate the free acid from the acetate form of the product; and (c) treating the free acid produced in Step (b) with a tertiary amine in isopropylacetate to precipitate the tertiary amine salt of Formula Ic.

7. The process of claim 6 wherein the solvent selected in Step (a) is acetonitrile and wherein the tertiary amine used in Step "c" is N,N-dimethyl-N-cyclohexylamine.

8. The process of claim 6 wherein the tertiary amine used in Step "c" is N,N-dimethyl-N-cyclohexylamine.

9. The process of claim 8 wherein the form of the compound of Formula Ib that is used in coupling Step (a) comprises at least about 90% ee of the (S,R,S) enantiomer of Formula (Ib-D).

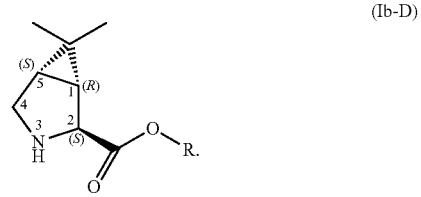

10. The process of claim 9 wherein the compound of Formula Ib comprises at least about 95% ee of the (S,R,S) enantiomer of Formula (Ib-D).

11. The process of claim 9 wherein the compound of Formula Ib comprises at least about 98% ee of the (S,R,S) enantiomer of Formula (Ib-D).

12. The process of claim 8 wherein the compound of Formula Ib comprises at least about 99% ee of the (S,R,S) enantiomer of Formula (Ib-D)

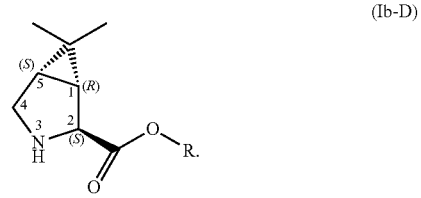

13. The compound of Formula Ic'

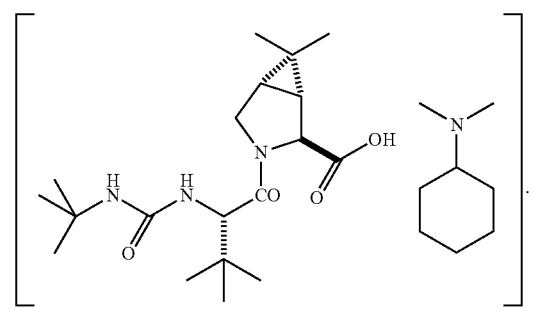

formula Ic'

* * * * *